United States Patent [19]

Persson

[11] Patent Number: 4,622,968
[45] Date of Patent: Nov. 18, 1986

[54] INSTRUMENT FOR THE TREATMENT OF RESPIRATORY OBSTRUCTION

[75] Inventor: Peter Persson, Upsala, Sweden
[73] Assignee: Economedica Sweden AB, Upsala, Sweden
[21] Appl. No.: 593,879
[22] Filed: Mar. 27, 1984

[30] Foreign Application Priority Data

Apr. 13, 1983 [SE] Sweden .................................. 8302061
Oct. 31, 1983 [SE] Sweden .................................. 8305978

[51] Int. Cl.$^4$ ........................ A61B 17/32; A61M 16/00
[52] U.S. Cl. ............................ 128/305.3; 128/200.26
[58] Field of Search ............... 128/305.3, 200.26; 604/165

[56] References Cited

U.S. PATENT DOCUMENTS

| 3,384,087 | 5/1968 | Brummelkamp | 128/305.3 |
| 3,395,711 | 8/1968 | Plzak | 128/200.26 |
| 3,766,916 | 10/1973 | Moorehead et al. | 604/165 |
| 3,916,903 | 11/1975 | Pozzi | 128/305.3 |

*Primary Examiner*—Michael H. Thaler
*Attorney, Agent, or Firm*—Witherspoon & Hargest

[57] ABSTRACT

The invention relates to an instrument for emergency treatment of i.a. respiratory obstruction in humans by percutaneous puncture of the trachea, the instrument comprising a body (2) having a through-passage (3) opening on one hand into a forward end (2c) of the body intended to be positioned against the neck of the patient, and on the other hand into a rear portion (2b) of the body a tube (6) coaxially provided in the passage in such a way that it protrudes from the forward end of the body and forms a continuation of the passage, the tube being intended to be introduced into the trachea of the patient, a stylet (7) retractably provided in the passage and/or in the tube (6) and adapted to protrude past the outer end of the tube (6) with its cutting point (7a) when in its fully inserted position. The tube (6) is preferably manufactured from a soft, resilient material and the rear end of the tube or the rear end of the passage and/or that end of the stylet which opens close to the rear portion of the body are provided with fittings (10) of standard size for permitting injection of pharmaceuticals by means of a conventional syringe and the rear end (2b) of the body consists of a tubular adapter formed integrally with the body and having standard dimensions for being connected to respiratory or anesthetic equipment.

10 Claims, 7 Drawing Figures

INSTRUMENT FOR THE TREATMENT OF RESPIRATORY OBSTRUCTION

BACKGROUND OF THE INVENTION

1. Field of the Invention

The invention relates to an instrument for emergency treatment of i.a. respiratory obstruction in humans, of the kind indicated in the preamble of the enclosed claim 1, and also relates to an appropriate use for the instrument.

2. Description of the Prior Art

Epiglottitis and other acute so called upper respiratory obstructions, which may e.g. be caused by a foreign object, allergic reactions, insect-bites in or injury to mouth and throat etc., are especially with children, but also with adults, dramatic problems. All health care facilities giving emergency care must have full capacity for correct and adequate treatment of such medical problems. Readiness must also be at hand within ambulance medical service, surgical medical service and military medical service. With the exception of specialist medical service the active readiness is, however, at present not satisfactory in practice since there is no simple, safe and appropriate instrument available for relieving the above mentioned conditions. Instruments have been developed such as the expensive and by many physicians dreaded cricothyroid membrane cutting device or coniotome (see e.g. Swedish patent application No. 7316352-9) which moreover is not recommended for use on small children under 5-6 years of age. Any other quite adequate instrument is neither available in practice nor discussed in the literature, which means that in an acute situation a great majority of physicians, not to mention other trained medical personnel, are left without any actual professional means of action and are rather thrown upon mere chance or their own more or less successful initiative. In the above discussed situations involving upper respiratory obstruction where the acute condition calls for an unobstructed airway and adequate respiratory assistance (in many cases the patient suffers from marked hypercapnia with weak or arrested spontaneous respiration) there is only one method available, namely tracheotomy, which is a potentially dangerous measure which almost without exception is performed in the operating rooms of hospitals. As a rule there is not enough time to perform a tracheotomy in cases of acute, high-grade upper respiratory obstruction, and this is generally true even if the patient already has arrived in an acute hospital offering emergency-surgery. Instead one of the five methods indicated below is used and these, at best, only provide for an adequate unobstructed airway but seldom or never provide for adequate respiratory assistance. Said five methods are:

1. Bag ventilation through mask, which is mostly impossible to perform in cases of acute epiglottitis or other forms of high-grade upper respiratory obstruction.

2. Tracheal intubation which even for the trained anesthesiologist often involves great difficulties or is regarded as impossible.

3. Cricothyroidotomy by means of a scalpel which is a surgical operation that in practice is used only as a last resort by specialists or physicians without any other alternative means of action. This method involves considerable danger and does not provide any immediate possibility for giving respiratory assistance, including oxygen supply.

4. Cricothyroidotomy by means of the above mentioned coniotome which, in principle, is the same course of action as under item 3. Here an instrument is used which makes the operation "semi-automatical" and which facilitates the introduction of a fine tube or the like. As mentioned above this emergency treatment is, however, medically unattractive to most physicians and in practice it is never used in spite of the fact that most medical students in Scandinavia receive instruction about use of the so called coniotome which is available as standard equipment in most health-care facilities offering acute care. A coniotome is only used as a last resort in an extreme emergency and moreover this method is not appropriate for use on children up to 5-6 years of age.

5. Percutaneous puncture of the cricothyroid membrane by means of a thick cannula, e.g. a larger type of cannula used for filling syringes or a large bore cannula for punction of the knee joint cavity. At present this is the most available method for children and of the invasive methods it is regarded to be the least dangerous one. Furthermore the expert opinion is that this method may give the patient a satisfactory possibility for respiration. The basis for this is that most upper respiratory obstructions form a one way valve above, at or just below the level of the vocal cords. Respiratory gas at positive pressure may be introduced through a relatively thin cannula and expiration is often possible past the respiratory obstruction, if necessary, by means of supportive compression of the thorax. Occasionally it is recommended to insert two needles in order to increase the cross-section area for inspiration. This method is however, associated with risks, e.g. injuries to the posterial wall of the trachea or to the oesophagus, mucous membrane mediastinal and subcutaneous emphysema among others. Worse is, however, the fact that the respiratory assistance which is often vital, cannot be given in a satisfactory manner. The physician is reduced to using mouth-to-cannula ventilation which is both impractical, difficult and ineffective. Oxygen may generally only be supplied if the patient is breathing spontaneously, and even then with an imminent danger of extinguishing the breathing reflexes of a patient in sleep, induced by marked hypercapnia, and the physician is once more reduced to using the above mentioned mouth-to-cannula ventilation in order to assist breathing. The position of the cannula may easily be inadvertently displaced and this may cause substantial injuries with bleeding down into the airways, since the cannula is nonresilient and its point sharp and non-flexible. It may also easily happen that the cannula is displaced from its proper position, which means that any respiratory assistance must be immediately stopped and the puncture repeated.

The patient, if not unconscious, must lie absolutely still if trauma from the hard and sharp needle is to be avoided. Thus it is evident that there is presently no safe, easy and efficient method available for providing free airway and for giving active respiratory assistance in the above mentioned acute situations.

Another example of a situation where it is presently not possible to give respiratory assistance without extremely serious consequences is in traffic accidents where a person suffering from a fractured cervical spine unconsciousness and/or difficulty in breathing, may remain sitting in the vehicle seat with the safety belt fastened and with his chin flexed down towards the chest. The only possibility for the ambulance personnel to give respiratory assistance is to flex the injured persons head backwards and to ventilate e.g. through a mask. If the cervical spine is fractured such a backward flexion of the head involves a very great danger of injuring the spinal cord which can cause the immediate death of the patient or leave a permanent neurological disability (e.g. tetraplegia).

In other situations involving respiratory arrest (e.g. Myocardial infarction with cardiac and respiratory arrest) great difficulties may often be encountered when conventional equipment is used for artificially ventilating the patient or giving him vital pharmaceuticals.

The objective of the invention is to provide an instrument of the kind mentioned in the introduction, eliminating the shortcomings of the above discussed prior methods and at the same time being relatively uncomplicated and thus simple and inexpensive to manufacture.

SUMMARY OF THE INVENTION

In accordance with the invention this objective is achieved by means of an instrument consisting of a body having a through-passage leading on one hand to a forward end of the body intended to be placed against the neck of the patient, and on the other hand to a rear portion of the body of the instrument, a tube secured in the passage in such a way that it protrudes from the forward end of the body and forms a continuation of the passage, the tube being intended for introduction into the trachea of the patient subsequent to puncturing the same by means of a needle or stylet which is retractably received in the passage and/or in the tube and which in its fully inserted position is adapted to protrude a predetermined distance past the outer end of the tube with its cutting point, and the tube being manufactured from a soft resilient material. Furthermore the rear end of the tube terminating in the instrument or the rear end of the passage and/or the rear end of the stylet are provided with fittings of standard size in order to permit injection of pharmaceuticals by means of a conventional syringe, and the rear portion of the body consists of a tubular adapter formed integrally with the body and designed with standard size for connection to conventional ventilation and anesthetic equipment (so called ISO-standard).

In relation to the above mentioned, presently used methods, such an instrument brings about i.a. the following advantages:

1. Percutaneous puncture of the trachea, especially through criocothyroid membrane, is considerably safer and simpler than incision (cricothyroidotomy). The danger of external or internal (to the lungs) bleeding is minimized and the puncture area is easily identified. The puncture does not render a subsequent tracheotomy or endotracheal intubation more difficult and the instrument may be kept in place and in operation during such procedures. Moreover the puncture technique is commonly accepted among medical personnel.

2. The soft tube or catheter reduces the risk of trauma in the subglottic space and finds its position therein in an optimal manner for providing an airway and for avoiding injuries.

3. The fitting on the rear end of the stylet permits injection of pharmaceuticals into the subglottic space during introduction of the instrument (e.g. local anesthetic and adrenalin). Furthermore, a plastic or glass syringe may be fitted to the rear end of the stylet in order to exactly determine, by means of aspiration or injection, employing the technique of loss of resistance, when the stylet has entered the subglottic space. In this way it is possible to effectively and safely avoid injuring the posterior wall of the trachea, the oesophagus or other structures.

4. The fitting at the rear end of the tube or the passage also permits injection of pharmaceuticals by means of a conventional plastic syringe once the instrument is in position and the stylet or needle retracted (e.g. local anesthetic or adrenalin—adrenalin injected directly into the trachea and lung has in the literature been reported to be at least as effective as an intravenous injection—or antiepileptic drugs in cases of status epilepticus caused by epilepsy or head trauma).

5. The standard size tubular adapter of the instrument fits connectors of standard type resuscitation bags and conventional anesthetic equipment. The so called Venturi-technique, which in recent years has been used i.a. in ambulances and for ear-nose-throat surgery may also advantageously be applied by means of the instrument. Unlike a common cannula fitting, the tubular adapter is easy to take hold of with the lips in the absence of ventilation equipment and in that manner air can be supplied to the patient by means of the mouth-to-instrument method. The design of the instrument as a unit easily permits controlled positive pressure ventilation with oxygen or air.

6. In principle the instrument may be introduced anywhere distal to the larynx where the trachea is accessible but percutaneous puncture of the cricothyroid membrane appears to be the safest method.

7. The instrument may be used immediately, without any special preparations, and may be used by all physicians and, in an emergency, also by other personnel sufficiently trained in first aid medicine, possibly also by informed laymen. The technique does not require any special surgical ability and is based upon training and knowledge which all physicians and many other medical categories are required to have.

8. Simplicity and safety; the possibility of controlled positive pressure ventilation of the patient with desired concentrations of oxygen and the possibility of, independent of accessible veins and without difficulty, injecting certain pharmaceuticals intratracheally during all types of respiratory arrests or obstructions, where conventional therapy has failed or has been dragging on; the method is bloodless and thus not repulsive or risky unlike all of the previously known methods employing other instruments.

9. The instrument may be used on all children as well as on adults regardless of weight.

10. The design of the instrument permits giving respiratory assistance to persons suffering from a fractured cervical spine without any need of moving the persons head at least not beyond a semi-forward flexed head position.

In accordance with alternative embodiments of the invention there is provided a possibility of injecting pharmaceuticals directly into the patient's trachea and lung at the same time as respiratory assistance is given with an optimal unsufflation of the lung at all times and there is provided an instrument comprising a minimum number of parts, which is universally applicable on small children and somewhat older children as well as on adults.

These alternative embodiments of the invention as well as other embodiments thereof are stated in the enclosed subclaims.

Finally the invention also relates to a favourable application of the instrument for injecting pharmaceuticals; such as adrenalin, atropine, lidocaine or antiepileptic drugs, directly into the trachea and lung of a patient. The uptake into the bloodstream of many drugs is very effective, as has been shown by myself and several other scientists. This is especially true for the invention, since it during controlled positive pressure ventilation maintains an optimal positive end expiratory pressure (PEEP) within the lung.

BRIEF DESCRIPTION OF THE DRAWING

In the following description, which is only intended to exemplify and not to restrict the invention, referred embodiments of the instrument, and certain preferable modifications thereof are described in connection with the enclosed schematic drawings in which.

DESCRIPTION OF THE PREFERRED EMBODIMENTS

Figure 1:
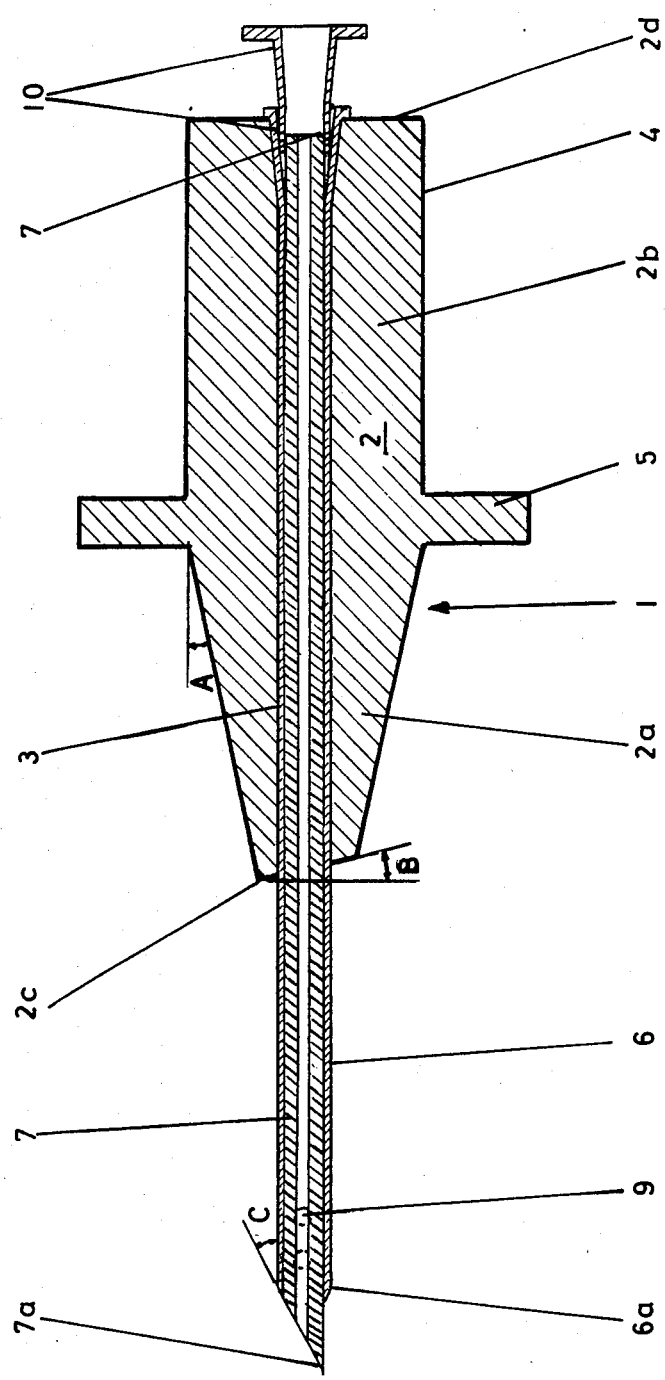
FIG. 1 is a side view, partially in section, of the instrument of the invention.

With reference to FIG. 1 a preferred embodiment of the instrument according to the invention is illustrated and as is clear therefrom the instrument 1 basically consists of a body 2 having a through-passage 3 opening on one hand into a forward end 2c of the body and on the other hand into a rear end 2d of the body. The length of the body 2 in its centre plane and measured on the upper and lower side thereof, is preferably (depending upon the angle (B) 45-55 mm and 25-45 mm respectively. The rear portion 2b of the body consists of a tubular adapter 4 which is formed integrally with the body and which is positioned substantially coaxially with at least that of the ends of the through-passage which opens into the rear end of the body. The adapter is provided with standard outer dimensions so that it may be connected to existing ventilator equipment, and according to the so called ISO-standard this presently means an outer diameter of 15 mm at the rear end 2d of the body. Furthermore, the body is provided with at least two wings 5 the purpose of which will be described more closely below. The wings as well as the adapter are preferably formed integrally with the body and the material which they consist of is a suitable hard plastic such as transparent polypropylene or rigid PVC or polystyrene.

Figure 3:
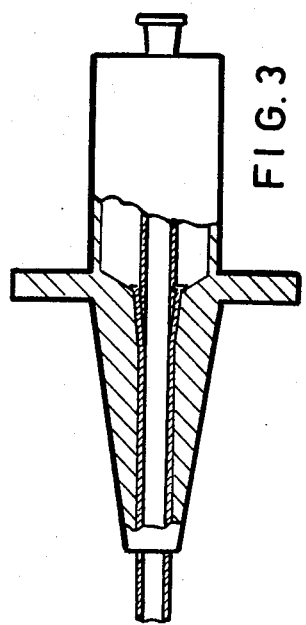
FIG. 3 illustrates, partially in section, an alternative embodiment of the instrument of the invention.
Figure 4:
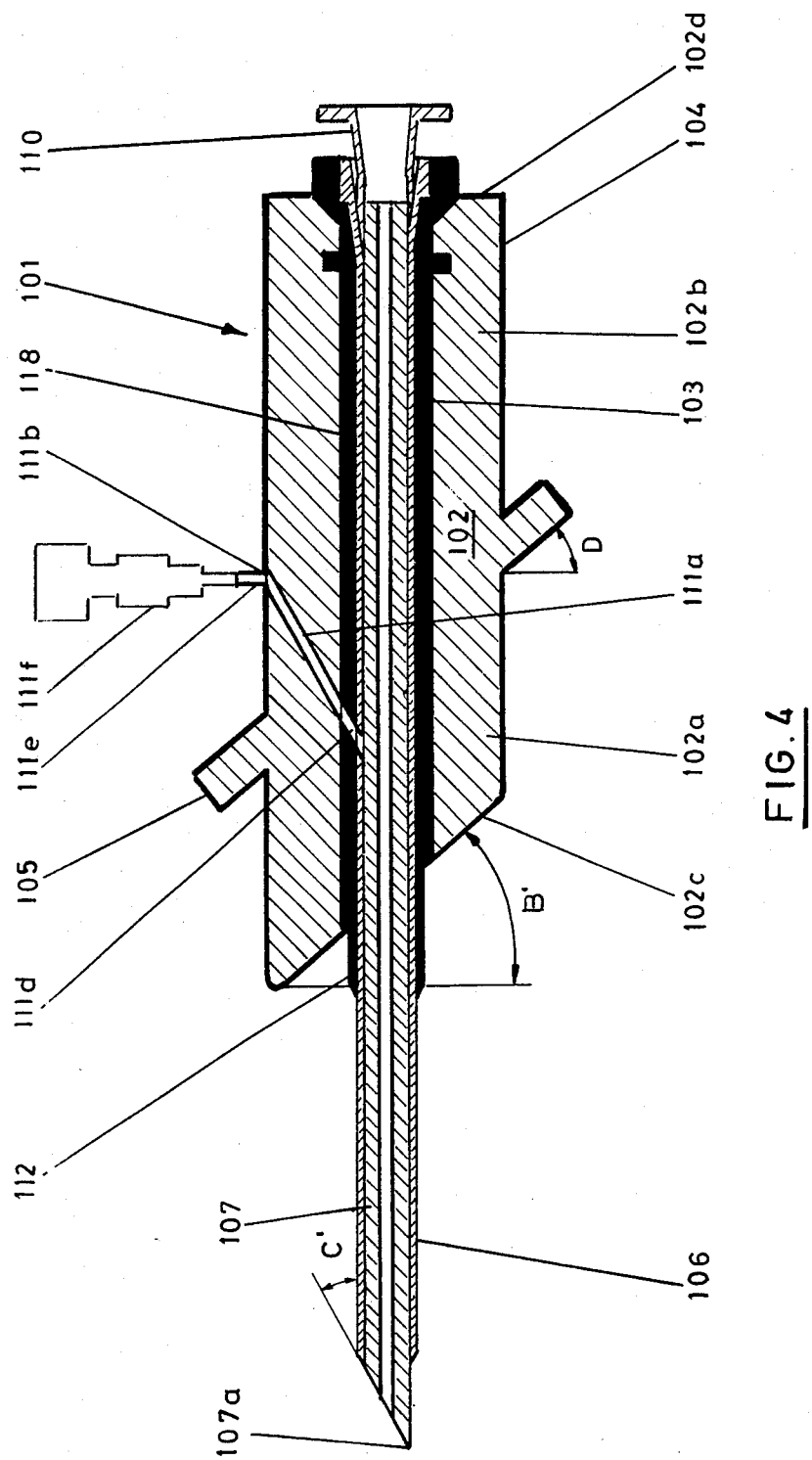
FIG. 4 is a side view, partially in section, of a further embodiment of the instrument.

The forward portion 2a of the body 2 may be tapered towards the forward end 2c thereof in order to avoid that the instrument interferes with the larynx when inserted. In this connection both the upper side and the lower side of the body may be inclined approximately 10°-15° (the angle A) in relation to the longitudinal axis of the instrument. The forward portion 2a may also be quite straight or may be inclined only at its lower side (see FIGS. 3a and 3c) so that it rests more securely on the neck of the patient with the larger surface. In that case only the lower side of the body may be inclined, for instance approximately 25°, in relation to the longitudinal axis of the instrument. In the embodiment including a straight catheter, the forward end 2c of the body may also be inclined 15°-60°, preferably 40°-60° (the angle B) in relation to a plane that is perpendicular to the longitudinal axis of the instrument, and the purpose of this is to facilitate a correct oblique introduction of the catheter into the trachea.

In the through-passage 3, a tube or a catheter 6 is secured in such a way that it protrudes from the forward end 2c of the body and forms a continuation of the passage 3. The forward, protruding portion of the catheter has a length of about 2.5-5 cm and is in the illustrated embodiment shaped as a straight continuation of the passage, but alternative designs are possible (see FIGS. 3a and 3c). Within the catheter 6 a stainless steel needle or stylet 7 is provided in such a way that the forward end 7a thereof protrudes past the outer end of the catheter. In use the catheter 6 is intended to be introduced into the trachea subsequent to the punction thereof by means of the outer cutting point 7a of the stylet. The stylet 7 which is preferably manufactured from stainless steel is for this cutting purpose sharpened to approximately 20°-45°, preferably 30°-40° (the angle C) at its forward end and may also be provided with a so called bevel cut edge or facet in order to be more easily inserted through the tissues. The cutting point may preferably be silicone-treated and it should be positioned in such a way that its cutting portion cuts crosswise, that is at 90° to the longitudinal axis of the trachea. The catheter may be manufactured from a non-rigid plastic, for instance ethylene-tetrafluor-ethylene (ETFE) or Teflon ® (PTFE) but polyurethane plastic which has a high biocompatibility and flexibility has been shown to be an especially suitable material, and is preferably cast integral with the passage 3, for instance by means of small projections on the Luer-fitting 10 described below. The catheter may be selectively positioned in the passage but preferably it should be positioned in such a way that it extends so far into the passage that its rear end is situated at a small distance from the rear end 2d of the body. In FIG. 3b an alternative embodiment is illustrated, where the adapter 4 is thin-walled, whereby the rear ends of the passage 3 and the catheter 6 open approximately into the middle of the body. The advantage of this is that the consumption of material will be less and the instrument will be lighter.

In order to facilitate the introduction of the catheter into the trachea its forward end 6a is chamfered in such a way that the thickness of the material in its wall is reduced from approximately 0.2 mm to approximately 0.05 mm along approximately 2-3 mm of its length.

The instrument may preferably by manufactured in two or more sizes, especially a children's model and an adult's model and in the children's model the catheter has an outer diameter of between 2.0 and 4.0 mm, preferably between 2.5 and 3.5 mm and an inner diameter of 1.5 to 3.5 mm, preferably 2.0 to 2.5 mm. The question whether a catheter of comparatively small dimensions is sufficent for the ventilation of children or not (possibly also for spontaneous respiration) has lately been discussed in Swedish as well as in foreign specialist press. This possibility has however not been generally accepted but has rather been doubted by many experts.

My own laboratory investigations on living pigs of different sizes, which have quite comparable requirements for supplied air volume, have unequivocally demonstrated that also small dimensions may be quite sufficient (the results from said investigations are presented at the National Convention of The Swedish Society of Medical Sciences on Nov. 30, 1983, in Stockholm, Sweden and at the 8th World Congress of Anesthesoilogists, Manila, Philippines on Jan. 25, 1984). If positive pressure ventilation with a resuscitation bag is used the effect increases substantially and will be sufficient for the provision of basal-condition ventilation also for adults. In the adult model the catheter has an outer diameter of 3.5 to 5.0 mm, preferably 3.9 to 4.5 mm and an inner diameter of 3.0 to 4.6 mm, preferably 3.0 to 4.0 mm. For both models the wall thickness of the catheter should, as has been mentioned above, be approximately 0.1 to 0.5 mm, preferably 0.2 to 0.3 mm.

In order to guarantee that the ventilation is not obstructed in case the forward opening of the plastic catheter inadvertently contacts the mucous membrane in connection with the introduction into the trachea or is plugged by mucus, the forward portion of the catheter is provided with a number of, preferably 2 to 4, side apertures 9 having a diameter of 1.0 to 1.5 mm.

The steel stylet should have an outer diameter corresponding to, or slightly smaller than, the inner diameter of the catheter, whereby it is crucial that the stylet may be withdrawn from the instrument without difficulty subsequent to the puncture of the trachea. The inner diameter of the stylet should at least in the forward portion thereof, closest to the cutting point, not exceed approximately 1 to 1.5 mm, which reduces the risk of occlusion during the introduction. This is of great importance since particles of tissue might otherwise get stuck in the stylet and fall down into the lungs of the patient together with the injection of pharmaceuticals through the stylet. Another advantageous effect of the relatively narrow inner passage of the stylet is that by said injection of pharmaceuticals through the stylet a spray- or jet-effect is achieved for the pharmaceuticals when it leaves the stylet, and this is especially important for instance when the introduction area is locally anesthetized and a uniform spread of the anesthetic (for instance Xylocain ®) is desirable. In order to reinforce this spray effect even further the inner passage may, at the point where it opens at the forward end of the stylet, be provided with or be shaped as a nozzle, for instance having the shape of a very sharp triangle (indicated in FIG. 2) or the shape of a cross. Furthermore, the stylet should have such a length that in its completely inserted position, that is with its cutting point protruding a predetermined distance past the forward end 6a of the catheter, its other end 7b protrudes approximately 5 to 10 mm from the adapter 4. In certain embodiments it is also preferable if the steel stylet is provided with a stop means (not shown) for preventing that its cutting point protrudes more than 3 to 6 mm from the forward end of the catheter.

The rear end of the stylet 7 is provided with a tapered fitting 10 that fits conventional syringes (a so called Luer-fitting) and a corresponding fitting 10 is also provided at the rear end of the passage 3 or alternatively at the rear end of the tube or catheter 6. In the latter case the fitting may be formed integrally with the tube. By means of these fittings it is possible to inject pharmaceuticals through the instrument both during the introduction of the instrument and once the instrument is in position with the steel stylet 7 withdrawn. In connection to the fitting 10 the steel stylet 7 may also be provided with a plastic cap in order to facilitate the withdrawal of the steel stylet subsequent to the punction of the trachea. In order to guarantee that the stylet is always correctly positioned in the instrument, i.e. is rotated to such a position that the cutting point is in its correct position for puncturing the trachea, the fitting at the rear end of the stylet is provided with a lug (not shown) which engages a corresponding notch in the tapered fitting at the rear end of the tube or of the passage when the stylet is in its correct position.

At the forward portion 2a of the body a fixation means (see FIG. 2) is provided for securing the instrument to the neck of the patient after the introduction. By a suitable embodiment the fixation means 12 consists of a pair of wings or plates 13 manufactured, for instance from transparent PVC, and provided on opposite sides of the body 2. The wings are preferably provided with hinges 14 (suitably in the shape of weakenings in the plastic material) in order to permit adaptation to the shape of the neck. On their forward side ("patient's side") the plates are provided with a layer of hard pressed plastic foam 15 having a double bonding gluing provided with a waxed paper foil which should be easily removeable in connection with use. Possibly, the plates may at their outer ends be provided with apertures (not shown) through which a cotton band may be run for fixing the instrument to the neck of the patient in a situation where bonding to the neck of the patient does not work in a satisfactory manner due to anatomical variations.

Possibly, a cylinder 16 of steel, or a thin rigid plastic may also be passed onto the protruding portion of the catheter and positioned against the forward end 2c of the body in order to strengthen this portion of the catheter so that it will not be compressed by the pressure from the tissues or buckled, and the cylinder should also be provided with a suitable collar 17 in order to prevent introduction into the trachea.

Figure 7:
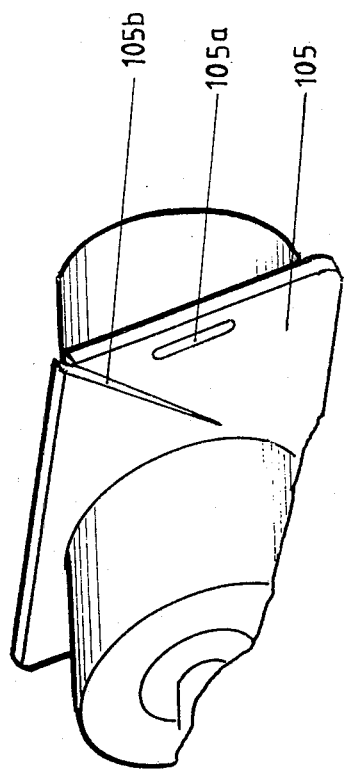
FIG. 7 is a partial front perspective view of the instrument of FIG. 4.

In FIGS. 4 to 7 an improved instrument according to the invention is illustrated. By this embodiment the body 102 is, mainly for reasons relating to the manufacturing thereof, designed having the same sectional shape along its full length, that is the forward portion 102a is shaped as a continuation of the rear tubular adapter 104, possibly having a smaller outer diameter in front of the wing which will be described below. In order to guarantee that the instrument 101 is placed in a correct position against the neck of the patient and rests firmly thereon when it has been introduced, the forward end of the body 102c is inclined at 40°-60° (the angle B') in relation to a plane perpendicular to the longitudinal axis of the instrument. As is especially clear from FIGS. 4 and 7 the instrument is by this embodiment provided with a single wing 105 extending around the full circumference of the body 102. Preferably, the wing 105 is shaped such that it is widest towards the sides and more narrow at the upper and lower portions respectively of the instrument. It has become evident that this shape of the wing 105 is especially suitable for a convenient or smooth handling of the instrument. Furthermore, it is clear that the wing 105 is inclined in relation to a plane perpendicular to the longitudinal axis of the instrument and preferably this angle D corresponds to the angle B' of the forward end 102c of the body. The intention of this inclination of the wing 105 is that it brings about a further stabilization of the instrument against the neck of the patient in those cases where the instrument is maintained in position by means of a cotton band run through the apertures 105a (only one is illustrated in FIG. 7) of the wing and brought round the neck of the patient. Instead of the apertures 105a, or as a supplement thereto, the wing may be provided with notches 105b into which the cotton band may rapidly be introduced so that it is secured at the bottom of the notches. In combination with the inclined wing the cotton band will thus maintain the instrument in a stable position whereas it would tend to tilt the instrument if the wing was straight.

Figure 5:
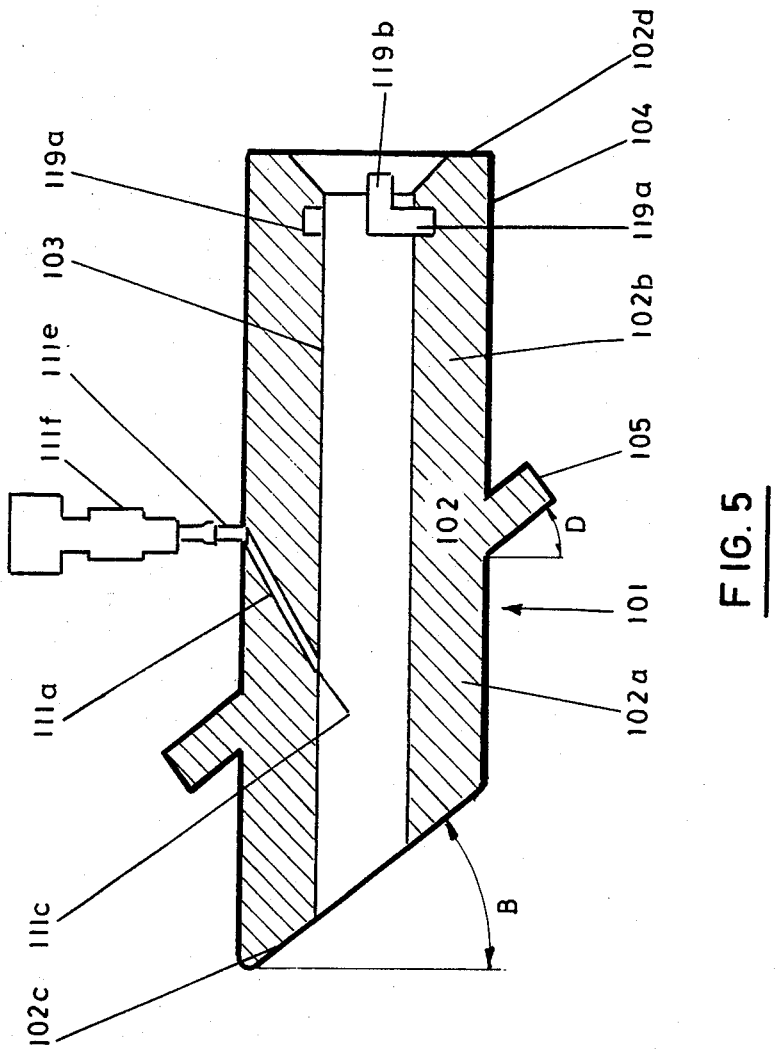
FIG. 5 is a view similar to FIG. 4 with the insert removed.
Figure 6:
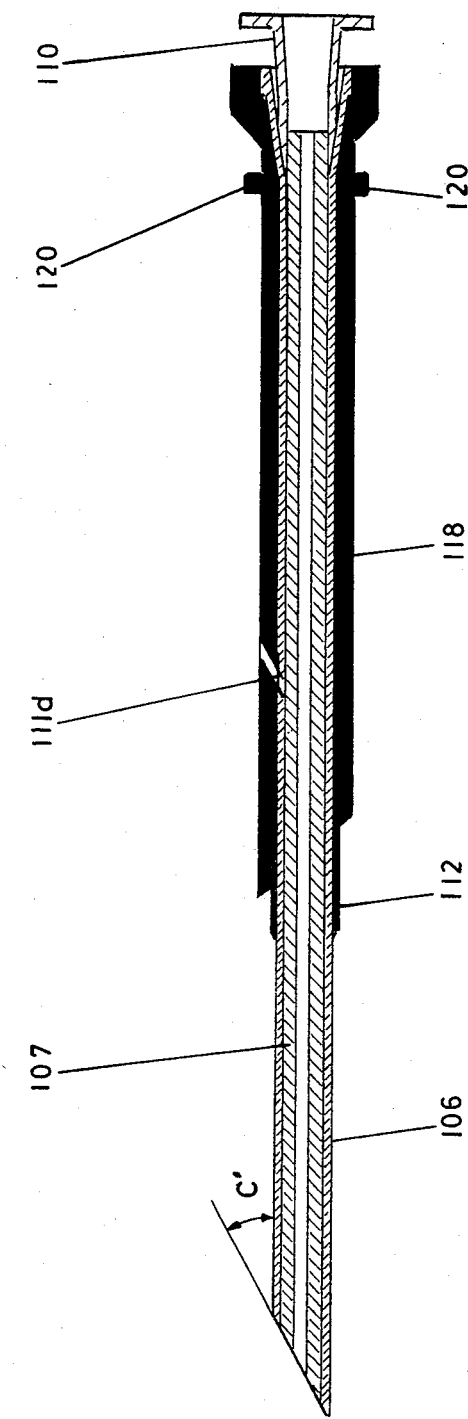
FIG. 6 illustrates the removed insert.

Compared to the embodiment illustrated in FIG. 1 the instrument 101 is provided with a wider central passage 103 into which an exchangeable insert or cartridge 118 is inserted. The tube or catheter 106 is secured in a central opening of the insert 118, and this catheter completely corresponds to the catheter 6 of the above described embodiment. This means that it receives the steel stylet 107 in a corresponding manner. In order to releasably fasten the insert 118 in the body 102 the insert is locked therein by means of a kind of bayonet mount which preferably consists of two grooves 119a formed in the rear portion 102b of the body, in connection to its rear end 102d. The grooves 119a are formed opposite each other along the periphery of the passage 103 and preferably extend along that periphery over approximately 90°. Furthermore, linear grooves 119b (one of which is illustrated in FIG. 5) are formed in the body and these grooves extend from the corresponding ends of the respective circumferential grooves 119a and to the rear end 102d of the body. In order to bring about locking, the insert is externally provided with two diametrically opposed lugs 120 which are guided along the linear grooves 119b and into the circumferential grooves 119a when the insert is introduced into the body. Subsequently, the insert is as a whole rotated in the passage 103 until the lugs 120 hit the bottom in the grooves 119a. In this manner, and in combination with the above described locking lug at the rear fitting of the stylet, a correct positioning of the cutting point 107a of the stylet in relation to the body is guaranteed. Naturally, it is also possible to use other locking means to achieve the releasable locking of the insert 118 in a proper position.

The advantage of this insert is that the body may be identical, that is the passage 103 may have the same dimensions, for all sizes of instruments required, that is instruments for small children, for somewhat older children and for grown-ups. In such cases different inserts or cartridges are employed which are provided with catheters 106 and stylets 107 of corresponding dimensions, and the only difference is that the thickness of the wall of the insert 118 varies for the different sizes of catheters and stylets. The outer dimension of the insert is always the same so that it fits into the passage 103 of the body 102.

Figure 2:
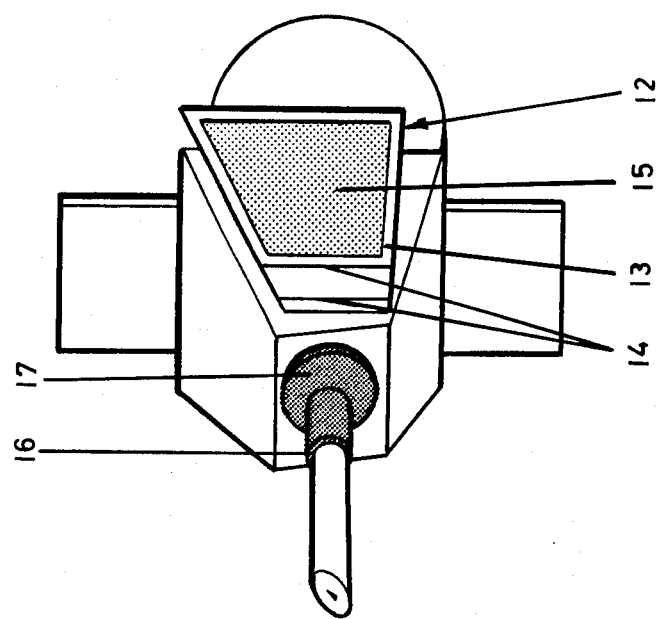
FIG. 2 is a front perspective view of the instrument of the invention.

By this embodiment the strengthening cylinder 16, which has been described with reference to FIG. 2, may suitably be formed integrally 112 with the insert 118 and thereby the portion 112 is preferably chamfered where it runs into the catheter 106.

The insert 118 is preferably manufactured from the same material as the body 102, but other materials may also be used.

For the purpose of permitting simultaneous injection of pharmaceuticals directly into the trachea of the patient when respiratory assistance is given, for instance through a respirator connected to the rear end 102d of the body, an injection channel 111a is formed through the body 102. In one end thereof the injection channel opens into an external orifice 111b situated approximately half-way along the upper side of the body with respect to its operating position. The other end of the injection channel 111a opens into an internal orifice 111c in the central passage 103 of the body. Furthermore, a continuation 111d of the injection channel 111a is formed in the insert 118 and in the catheter 106. This continuation 111d of the channel 111a is positioned in such a way that when the insert is introduced into the body and is locked in a proper position therein the continuation communicates with the injection channel 111a. In connection with the junction between the channel 111a and its continuation 111d one or both of the channels may preferably be widened so that a proper communication between the channels is always guaranteed, independent of possible manufacturing tolerances.

At the orifice 111b of the injection channel 111a there is provided a connecting tube 111e of stainless steel or any other suitable material, onto the free end of which a thin plastic hose is passed which in turn is connected to a Luer-Lock-adapter 111f through which pharmaceuticals may be injected into the connecting tube 111e, the injection channel 111a, the channel 111d and into the catheter 106. Preferably, the injection channel 111a and its continuation or extension 111d form an acute angle with the longitudinal axis of the instrument, the angle pointing towards the forward end of the instrument. This arrangement provides the most advantageous flow-path for the injection from the channel to the catheter and from there into the patient.

It should also be understood that the embodiment of FIG. 1 just as well may be provided with such an injection channel for permitting simultaneous injection and ventilation.

In certain situations, it may be necessary to connect an adapter tube to the adapter of the instrument so that a larger space is obtained for connecting respiration equipment. This especially concerns children where the space between the chin and the upper portion of the chest is limited. Said adapter tube may be straight or angled. The straight tube may especially be employed if the patient lies flat on his back or for small children, while the angled tube is appropriate to use if the patient lies in the NATO-position. Both the angled and the straight tubes should have such dimensions that one end thereof fits the adapter of the instrument and the other end fits the respirator equipment. The adapter tubes are preferably manufactured from a rigid plastic, possibly from the same material as the instrument, and may be provided with a marking (for instance "patient" and "respirator" in the respective ends) in order to facilitate the connection.

The instrument is intended to be used in the following manner: The head of the patient is, if possible, flexed backwards to a maximum and the instrument is preferably grasped with a three-point grip, for instance with the thumb on the stylet fitting, the index finger around one of the wings and the middle finger around the other wing. If a fractured servical spine is suspected the instrument is introduced into the trachea of the patient without any preceding backward flexion of the patient's head. The cricothyroid membrane is palpated with the index finger of the other hand. The instrument should be positioned with the marking (for instance "Top") on the upper side of the body facing away from the chin or neck of the patient. If necessary, local anesthetic with an adrenalin additive is given on the spot of the introduction and into the trachea. The instrument is properly positioned and is pushed through the skin and through the cricothyroid membrane. In order to test whether the point of the stylet has reached into the trachea or not, a syringe may be used for aspirating through the fitting of the stylet. When it has been established in this manner that the point of the stylet has punctured the trachea the steel stylet is carefully withdrawn at the same time as the plastic catheter is pushed inwardly-downwardly. The instrument is moved further on until the forward end 2c of the body rests against the skin of the neck. The instrument is fixed to the neck of the patient by means of the fixation means and then an adapter tube is connected if necessary. By the embodiment according to FIGS. 1 to 3 necessary injections should however have been given beforehand by means of a syringe and through the fitting at the rear end of the passage. By the embodiment according to FIGS. 4 to 7 injections may be made through the injection channel 111a in synchronization with inflation of the patient's lungs. Finally, respiration equipment is connected (for instance an Ambu or Laerdal or Ruben resuscitation bag or a respirator with a suitable valve and with oxygen supply) directly to the adapter of the instrument or through the adapter tube.

Even in situations where respiratory assistance is not absolutely vital the instrument may advantageously be used solely for injecting pharmaceuticals directly into the trachea and lung of the patient, that is in such situations where a rapid absorption of pharmaceuticals to the blood is desirable. Examples of such situations are in connection with status epilepticus or cardiac arrest, where an intravenous line may be difficult to establish due to shock and collapsed veins.

The instrument is meant to be sterilized and packed for single use and regarding the embodiment illustrated in FIGS. 4 to 7 one body is preferably packed together with two or possibly three inserts having different sized catheters and stylets. Thereby, the body may be combined with a desired insert for patient to be treated and this may be carried out rapidly and easily using a minimum number of parts. The insert 118 and/or the fitting 110 may preferably be colour marked in order to clearly indicate the dimension of the catheter. The instrument is intended to be used in emergency rooms or operating theatres, in ambulances and elsewhere while awaiting definite treatment at an emergency hospital. As mentioned above such definite treatment, for instance tracheotomy, may preferably be performed with the instrument in position and operating.

Although preferred embodiments of the invention have been described above it should be understood that a great number of modifications may be carried out without departing from the basic teachings of the invention, and such modifications may for instance include choices of materials and adjustments of certain angles and sizes. Such modifications do naturally also include transferring the different structural solutions between the different embodiments described above, and this especially concerns the external design of the body and the shape of the wing (wings). Thus, it should be understood that the scope of the invention is to be determined solely by the enclosed patent claims.

I claim:

1. Instrument for providing an unobstructed airway and for giving active respiratory assistance in acute situations by percutaneous puncture of the cricothyroid membrane, comprising a body having a through-passage opening on one hand into a forward end of the body intended to be positioned against the neck of the patient and on the other hand into a rear portion of the body, the rear portion of the body comprising a tubular adapter formed integrally with the body and having standard dimensions for connecting the same to respiratory or anesthetic equipment, a tube secured coaxially within the passage in such a way that it protrudes from the forward end of the body and forms a continuation of the passage, the tube having an outer dimension smaller than the cross dimension of the passage and being stationary in an insert the outer diameter of which substantially corresponds to the cross section diameter of the passage and which is retractably positioned in the passage, the tube being intended for introduction into the trachea of the patient and being manufactured from a soft, resilient material, a puncture means retractably provided in the tube and adapted to protrude past the outer end of the tube with its cutting point when in its fully inserted position, the puncture means having an outer diameter about equal to the inner diameter of the tube and comprising an inner passage which at least along a portion thereof has a cross section diameter not exceeding approximately 1 to 1.5 mm, a channel extending from an external orifice at the outside of the body and into the inside of the tube, and fittings of standard size being provided at least at the end of the puncture means close to the rear portion of the body, the fittings permitting an exact determination, by means of aspiration, of when the puncture means has entered the subglottic space and also permitting injection of pharmaceuticals by means of a conventional syringe.

2. Instrument according to claim 1, wherein the insert may be releasably secured in a fixed position within the passage by means of a mount.

3. Instrument according to claim 1, wherein the front surface of the body is inclined 15° to 60°, preferably 40° to 60° in relation to a plane perpendicular to the longitudinal axis of the instrument, and wherein the passage and the tube extend substantially along the longitudinal axis of the instrument.

4. Instrument according to claim 1, wherein the fittings have a tapered internal shape adapted for conventional syringes having a so called Luer-fitting.

5. Instrument according to claim 1, wherein the adapter is dimensioned according to ISO-standard, having an outer diameter of 15 mm at the rear end of the body and having a slightly tapered shape in accordance with said standard.

6. Instrument according to claim 1, wherein tubular means couples the external orifice with a Luer-Lock-adapter and wherein the channel forms an acute angle with the longitudinal axis of the instrument, said angle pointing towards the forward end of the instrument.

7. Instrument according to claim 1, wherein the body is provided with at least one wing at its outer surface, said wing being inclined at an angle corresponding to that of the front surface of the body in relation to a plane perpendicular to the longitudinal axis of the instrument.

8. Instrument according to claim 1, wherein fixation means consisting of a pair of plates are provided close to the forward end of the body, said plates being pivotally connected to the body and on one side thereof being provided with a layer of hard pressed plastic foam having a double bonding gluing.

9. Instrument according to claim 1, wherein the tube close to the body is provided with a strengthening cylinder formed integrally with the insert.

10. Instrument for providing an unobstructed airway and for giving active respiratory assistance in acute situations by percutaneous puncture of the cricothyroid membrane, comprising a body having a through-passage opening on one hand into a forward end of the body intended to be positioned against the neck of the patient and on the other hand into a rear portion of the body, the rear portion of the body comprising a tubular adapter formed integrally with the body and having standard dimensions for connecting the same to respiratory or anesthetic equipment, a tube secured coaxially within the passage in such a way that it protrudes from the forward end of the body and forms a continuation of the passage, the tube being intended for introduction into the trachea of the patient and being manufactured from a soft, resilient material, a puncture means retractably provided in the tube and adapted to protrude past the outer end of the tube with its cutting point when in its fully inserted position, the puncture means having an outer diameter about equal to the inner diameter of the tube and comprising an inner passage which at least along a portion thereof has a cross section diameter not exceeding approximately 1 to 1.5 mm, a channel extending from an external orifice at the outside of the body and into the inside of the tube, and fittings of standard size being provided at least at the end of the puncture means close to the rear portion of the body, the fittings permitting an exact determination, by means of aspiration, of when the puncture means has entered the subglottic space and also permitting injection of pharmaceuticals by means of a conventional syringe, and a strengthening cylinder passed onto the tube and positioned close to the body, the cylinder in turn being provided with a collar preventing the strengthening cylinder from being introduced into the trachea.

* * * * *